US007799124B2

(12) United States Patent
Subramanian et al.

(10) Patent No.: US 7,799,124 B2
(45) Date of Patent: Sep. 21, 2010

(54) PROCESS FOR TREATING INORGANIC PARTICLES VIA SINTERING OF SINTERABLE MATERIAL

(75) Inventors: Narayanan Sankara Subramanian, Hockessin, DE (US); Russell Bertrum Diemer, Jr., Wilmingon, DE (US); Pratibha Laxman Gai, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 1025 days.

(21) Appl. No.: 11/392,369

(22) Filed: Mar. 29, 2006

(65) Prior Publication Data

US 2006/0275227 A1 Dec. 7, 2006

Related U.S. Application Data

(60) Provisional application No. 60/669,099, filed on Apr. 7, 2005.

(51) Int. Cl.
*C04B 14/00* (2006.01)
*C09C 1/36* (2006.01)
*A61K 8/18* (2006.01)
*A61Q 17/04* (2006.01)

(52) U.S. Cl. ................ 106/400; 424/59; 977/926; 106/401; 106/436

(58) Field of Classification Search ................ 106/400; 424/59; 977/926
See application file for complete search history.

(56) References Cited

U.S. PATENT DOCUMENTS 3,640,744 A * 2/1972 Dietz et al. ................. 106/438
3,856,929 A 12/1974 Angerman et al.
4,050,951 A 9/1977 Piccolo et al.
4,124,913 A 11/1978 Rosendall
4,986,853 A * 1/1991 Kieser ........................ 106/504
5,221,334 A 6/1993 Ma et al.
5,340,393 A 8/1994 Jacobson
5,562,764 A 10/1996 Gonzalex
5,759,511 A 6/1998 Diemer, Jr. et al.
5,886,069 A * 3/1999 Bolt ........................... 523/223
5,922,120 A 7/1999 Subramanian et al.
6,632,275 B1 * 10/2003 Schoen et al. ............... 106/404

(Continued)

FOREIGN PATENT DOCUMENTS

EP 0 032 426 B1 11/1983

(Continued)

OTHER PUBLICATIONS

Y. Xiong et. al., Formation of Agglomerate Particles by Coagulation and Sintering—Part II. The Evolution of the Morphology of Aerosol-Made Titania, Silica and Silica-Doped Titania Powders, J. Aerosol. Sci., 1993, vol. 24:301-313.

(Continued)

*Primary Examiner*—Jerry Lorengo
*Assistant Examiner*—Joseph V Micali

(57) ABSTRACT

The present disclosure relates to a process for making treated inorganic particles by vapor phase deposition of surface treatments on the particle surface by reacting inorganic particles, typically titanium dioxide particles, with a composition comprising a sinterable material and a liquid medium at a temperature sufficient to evaporate the medium and release the sinterable material as aerosol particles. The aerosol particles sinter and form a treatment on the surfaces of the inorganic particles.

40 Claims, 4 Drawing Sheets

U.S. PATENT DOCUMENTS

| | | | |
|---|---|---|---|
| 6,660,793 | B1 | 12/2003 | McIntyre et al. |
| 6,852,306 | B2 | 2/2005 | Subramanian et al. |
| 2003/0051635 | A1 * | 3/2003 | Subramanian et al. ...... 106/437 |
| 2003/0108667 | A1 | 6/2003 | McIntyre et al. |

FOREIGN PATENT DOCUMENTS

| | | |
|---|---|---|
| GB | 689123 | 3/1953 |
| WO | WO 96/36411 A1 | 11/1996 |

OTHER PUBLICATIONS

P.L. Gai, Direct Probing of Gas Molecule-Solid Catalyst Interactions on the Atomic Scale, Advanced Materials, 1998, pp. 1259-1263, vol. 10.

* cited by examiner

PROCESS FOR TREATING INORGANIC PARTICLES VIA SINTERING OF SINTERABLE MATERIAL

CROSS-REFERENCE TO RELATED APPLICATIONS

This application claims the benefit of U.S. Provisional Application No. 60/669,099, filed Apr. 7, 2005 which is incorporated by reference in its entirety.

BACKGROUND OF THE INVENTION

The present disclosure relates to the production of treated inorganic particles. While this disclosure can be used to produce a range of particles, advantageously, this disclosure provides a route to a durable grade pigment, without the necessity of depositing surface treatments on pigment particles by wet treatment methods.

U.S. Pat. No. 5,340,393 discloses processes for depositing dense amorphous silica coatings on inorganic particles, especially metal oxides via wet treatment methods. The inorganic particles include oxides of titanium, magnesium, calcium, barium, strontium, zinc, tin, nickel, and iron as well as complex oxides such as mica, cordierite, enorthite and pyrophyllite. The inorganic particles also include carbonates and sulfates such as those of calcium, barium and strontium.

Titanium dioxide is typical of an inorganic particle that is frequently treated prior to incorporation into end use applications. Titanium dioxide pigment particles, produced by either the chloride or the sulfate process, are processed in one or more wet treatment operations to deposit metal oxides on the surface of the pigment in order to optimize the pigment properties of dispersion, optical spacing or durability. Deposits of aluminum oxide or combinations of aluminum oxide and silicon dioxide, used alone or in combination with other oxides, are typical constituents of commercial titanium dioxide pigment. Such surface treatments are deposited through precipitation of the desired metal oxide in a wet chemical reaction. Thus, the base pigment, that is, the titanium dioxide particles produced at the exit point of the oxidizer in the chloride process or after calcination in the sulfate process, must be washed and processed through one or more wet treatment steps. Wet treatment is then followed by washing, drying and grinding to produce a product suitable for use in for example, exterior coatings and plastics products.

In the chloride process, an oxygen-containing gas is reacted with titanium tetrachloride ($TiCl_4$) at temperatures ranging from 900° C. to 1600° C. in a vapor phase. The resulting gaseous suspension of $TiO_2$ particles and free chlorine are discharged from the reactor and must be quickly cooled in a conduit, i.e., a flue, so that undesired $TiO_2$ particle growth is prevented and particle agglomeration is minimized.

Processes to influence the titanium dioxide crystal formation and/or growth by addition of chemical agents in the oxidizer of the chloride process are taught in British Patent 689,123, and U.S. Pat. Nos. 3,856,929; 4,124,913; and 5,562,764.

So-called vapor or dry process to deposit surface treatments on the pigment in the oxidation step are taught in U.S. Pat. No. 4,050,951; PCT published patent application WO 96/36411; and European Patent 0 032 426. In U.S. Pat. No. 4,050,951 post treatment hydrolysis is taught. The disadvantage in this system is that the treatment step is a separate stage in the overall process, following oxidization that requires the separation of base pigment from the oxidation product, then grinding followed by hydrolysis at temperatures lower than those temperatures present in the oxidizer.

PCT application WO 96/36441 teaches a vapor phase treatment process requiring that the silicon tetrachloride addition must be made at a temperature of more than 1300° C. This application further teaches that the addition of metal halides can be made in any sequence and at any point in the reactor.

European Patent 0 032 426 teaches a post treatment of titanium dioxide particles in a fluid bed reactor. This process requires an activation step where the titanium dioxide particles are contacted with metal chlorides followed by a hydrolysis to convert residual chlorides to oxides and oxide hydrates.

U. S. Pat. Nos. 5,922,120 and 6,852,306 advance the technology of vapor or dry process to deposit surface treatments on $TiO_2$ particles. These processes can produce durable $TiO_2$ pigments with a very high percentage of particles treated. However, these processes rely on use of volatile silicon halides as the silica source for treating particles.

There is a need for a process to make a treated inorganic particle without use of wet treatment or volatile silicon halides, which may be difficult and/or hazardous to handle. In one particular example, there is a need for a process to produce a durable grade commercial titanium dioxide pigment of acceptable gloss and carbon black undertone (CBU) without use of wet treatment or volatile silicon halides. There is also a need to avoid the cost and additional processing required in the typical wet treatment operation. The present disclosure meets these needs.

BRIEF SUMMARY OF THE INVENTION

The present disclosure provides a process for the making of a treated inorganic particle, for example, a durable grade pigment product, by contacting inorganic particles with particles of a sinterable material capable of forming a coating layer on the surface of the inorganic particle. Especially suitable as the inorganic particle are metal oxides, typically, metal oxides which are produced by flame oxygenation processes such as, titanium dioxide, fumed silica and zinc oxide. Thus, the present disclosure is a process for producing inorganic particles bearing a surface treatment, the process comprising:

contacting inorganic particles with a composition comprising a sinterable material and a liquid medium, at a temperature sufficient to (1) evaporate the liquid medium and release the sinterable material as aerosol particles and (2) cause the aerosol particles to sinter to form a coating on the inorganic particles.

Typically, the contacting step occurs in an oxygenation process to produce inorganic particles, such as into the oxidation unit of a chloride process titanium dioxide plant. Therein, conveniently and typically titanium dioxide particles are provided by reacting titanium tetrachloride vapor and aluminum chloride with at least a stoichiometric amount of oxygen in a plug flow reactor to form a product stream comprising titanium dioxide particles. It is also typical, as part of the chloride process, before the introduction of a composition comprising a sinterable material to the reactor, that at least 97% of the titanium tetrachloride has been converted to titanium dioxide, more typically at least 98%, and most typically at least 99% of the titanium tetrachloride has been converted to titanium dioxide. It is further typical that aluminum trichloride is added in an amount sufficient to provide an aluminum oxide content of at least about 1% by weight, based on the total weight of the product.

The process can be advantageously used to produce durable pigments, for example, when the inorganic particle is titanium dioxide of a pigmentary particle size and when the sinterable material is silicon dioxide. A durable titanium dioxide pigment has a surface treatment layer comprising silicon dioxide in an amount of at least about 1.2% by weight of the pigment, wherein at least 85% of the pigment particles are completely covered by a uniform layer comprising amorphous silicon dioxide and a mixture of amorphous silicon dioxide and amorphous aluminum oxide when the titanium dioxide pigment has been produced by the chloride process with addition of aluminum trichloride, and wherein the pigment particles are substantially free of debris.

Similarly, the process of this disclosure can be incorporated into oxygenation processes to prepare fumed silica and zinc oxide.

BRIEF DESCRIPTION OF THE DRAWING(S)

DETAILED DESCRIPTION OF THE INVENTION

Figure 1:
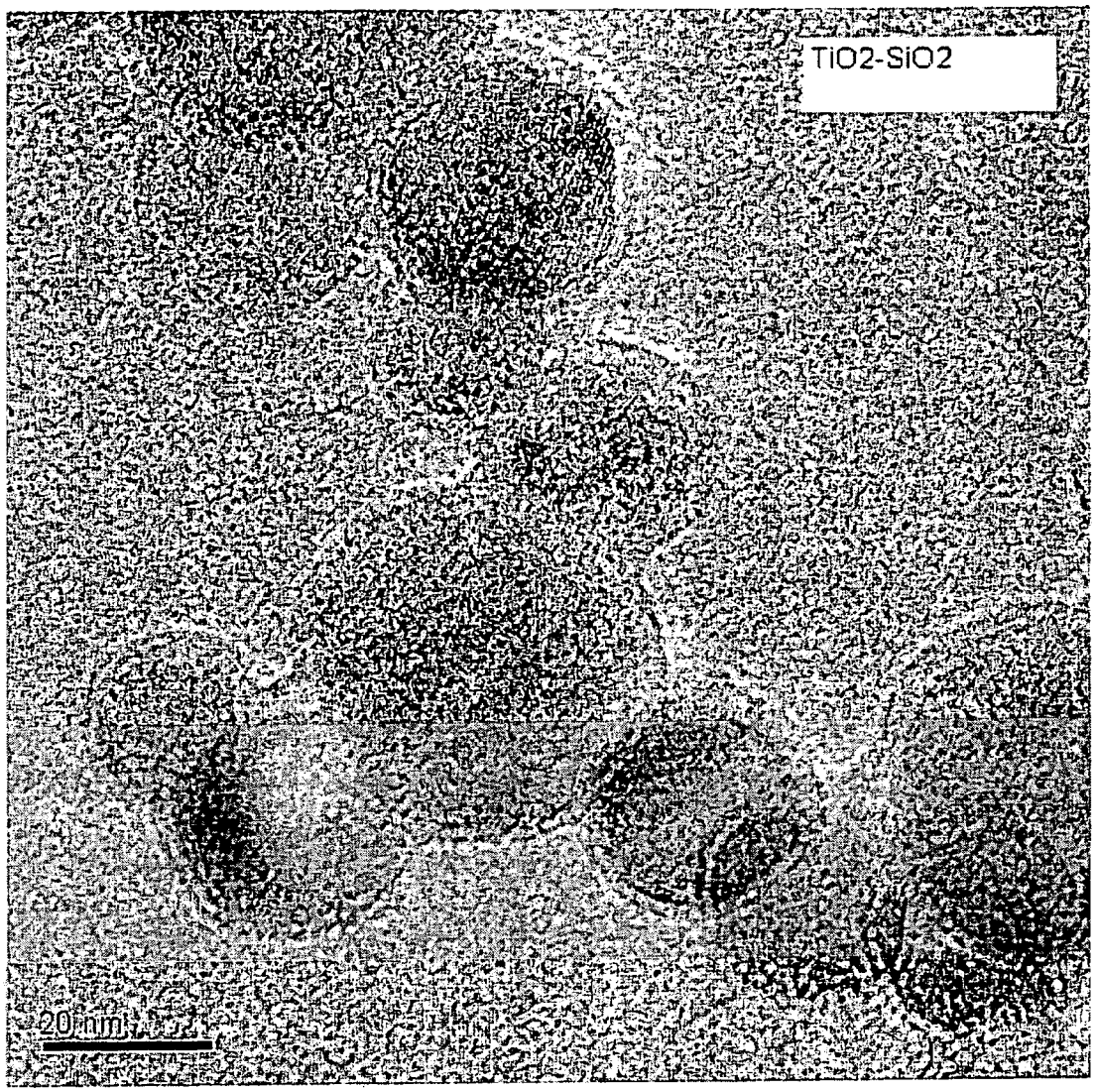
FIG. 1 is an electron micrograph of the titanium dioxide pigment particles produced in Example 1.

It should be noted herein that silica and silicon dioxide are used interchangeably herein, both referring to a composition of $SiO_2$.

The present disclosure provides a process for making treated inorganic particles by vapor phase deposition of surface treatments on the inorganic particle surface, the process comprising the steps of: contacting inorganic particles with a composition comprising a sinterable material and a liquid medium at a temperature sufficient to (1) evaporate the liquid medium and release the sinterable material as aerosol particles and (2) cause the aerosol particles to sinter to form a coating on the inorganic particles.

The process of this disclosure can be used to apply a treatment to a wide variety of inorganic particles, including oxides, carbonates, sulfates, titanates, arsenides, sulfides, selenides, phosphides and combinations of two or more thereof. Representative examples of oxides include oxides of titanium, magnesium, calcium, barium, strontium, zinc, tin, nickel, silicon, and iron. Other metal oxides include oxides of selenium, tungsten, ruthenium, tin, tantalum, silver, iridium, molybdenum, niobium, indium, cadmium, hafnium, zirconium, manganese, copper (I), vanadium, chromium (VI), yttrium, germanium, and mixed oxides, such as aluminosilicate and $Ti_xZr_{1-x}O_2$ wherein x is between 0 and 1.

Representative examples of carbonates and sulfates are carbonates and sulfates of calcium, barium, and strontium.

Representative of titanates are titanates of barium, strontium, and calcium.

Representative of arsenides is gallium arsenide.

Representative of sulfides are sulfides of zinc, molybdenum, cadmium, indium, copper, tungsten, bismuth, mixed sulfides of cadmium and zinc.

Representative of selenides are selenides of cadmium, zinc, indium, and tungsten.

Representative of phosphides are phosphides of indium and gallium.

Additional representative examples include diamond, germanium telluride, cadmium telluride, compounds of homopolyanions such as $W_{10}O_{32}^{4-}$ and heteropolyanions such as $XM_{12}O_{40n-}$ or $X_2M_{18}O_{62}^{7-}$ wherein X is Bi, Si, Ge, P or As; M is Mo or W and n is an integer from 1 to 12.

Typical are particle oxides selected from the group of titanium dioxide, zinc oxide and fumed silica. Still more typical is a process wherein contacting step occurs in an oxygenation process to produce the inorganic particles. Most typically, the inorganic particle is titanium dioxide.

The inorganic particles can be of any particle size suitable for a desired application. For some inorganic particles they are particularly useful as pigments. By "pigment", it is meant herein to describe inorganic particles of pigmentary size, that is, having an average particle size in the range of about 200 to about 1000 nanometers, typically, about 200 to about 500 nanometers.

The inorganic particles may also be of subpigmentary particle size. Subpigmentary particles, also referred to as nanosized particles, typically have an average size ranging from about 10 to about 200 nanometers, typically from about 20 to about 150 nanometers.

The process of this disclosure can be used to apply one or more treatments comprising one or more sinterable materials. By a "sinterable material" it is meant, a material that, under the process conditions of this disclosure, will form aerosol particles, which coalesce and form a coherent mass, treating the surface of an inorganic particle. Sinterable materials are typically inorganic oxides and mixed oxides. Representative oxides include silica, alumina, phosphorous oxide, boron oxide, magnesium oxide, niobium oxide, germanium oxide, zirconium oxide or zinc oxide. Representative mixed oxides include aluminosilicate, aluminophosphate, boron aluminate glass, borosilicate glass or silica-phosphates glass. Where the metal oxide forms an acid upon mixing with water, it is typical that the temperature is sufficient to dehydrate the acid.

The sinterable material is typically present in the composition in the form of particles. The particle size can be any particle size capable of sintering to form a treatment on the surface of the inorganic particle. The treatment may be continuous, discontinuous, uniform or non-uniform depending on the sintering conditions. The typical particle size relates to the temperature at which the inorganic particles are contacted with the sinterable material composition and on the size of the inorganic particles. Higher temperatures will support larger particle sizes for sintering to form a uniform treatment of sinterable material on the surface of the inorganic particles.

Generally, the sinterable material will be in the form of colloidal particles. By "colloidal particles" it is meant particles having a typical size of less than 100 nanometers. Typically, the sinterable material has a particle size of at least 5 nanometers. More typically, the sinterable material particles are 50 nanometers or less in size, still more typically 30 nanometers or less in size and most typically 20 nanometers or less in size. For example, a typical composition comprising a sinterable material is a silicon dioxide slurry comprising silicon dioxide particles of 10-20 nanometers in size and water as the liquid medium. Smaller particles of sinterable material, e.g., 5-10 nanometers in size, are typical for subpigmentary inorganic particles.

Typically the composition comprising the sinterable material is a slurry comprising colloidal particles of the sinterable material and the liquid medium is a slurry medium. More typically, the sinterable material is silica or alumina. Colloidal slurries comprising alumina and silica are readily available commercially. Most typically, the sinterable material is silica, which can be used to provide durable treatments on the surface of inorganic particles.

The liquid medium is any suitable medium that is volatile, that is, will evaporate to enable generation of aerosol particles of the sinterable material under conditions in which the composition comprising a sinterable material is contacted with the inorganic particles. Suitable liquid media include water and solvents compatible with the inorganic particle and sinterable material, such as titanium tetrachloride.

In a typical embodiment, the inorganic particles are titanium dioxide particles and the sinterable material is silicon dioxide. Typically titanium dioxide particles are provided by oxidation of titanium tetrachloride, that is, by the chloride process for producing $TiO_2$. This process comprises reacting titanium tetrachloride vapor stream, and, typically a titanium tetrachloride vapor stream comprising aluminum chloride, with at least a stoichiometric amount of oxygen in a plug flow reactor to form a product stream comprising titanium dioxide particles. It is also typical when producing $TiO_2$ by the chloride process that, before the introduction of the composition comprising sinterable particles, at least 97% of the titanium tetrachloride has been converted to titanium dioxide, more typically at least 98%, and most typical that at least 99% of the titanium tetrachloride has been converted.

The sinterable composition may be contacted with the $TiO_2$ particles in one or more stages or steps. Typically, in the chloride process, the composition is contacted with the $TiO_2$ particles, that is, introduced into the reactor at one or more points downstream of the point where the titanium tetrachloride and oxygen were contacted, where at least 97% of the titanium tetrachloride has been converted (no more than 3% unreacted titanium tetrachloride) to titanium dioxide.

Typically, $TiO_2$ particles are treated with silicon dioxide to provide a durable pigment. The term "durable" as used herein means a pigment suitable for exterior architectural treatments and automotive refinish or color coat/clear coat OEM finishes. $TiO_2$ particles of pigmentary size have an average particle size in the range of about 200 to about 1000 nanometers, typically, about 200 to about 500 nanometers. Generally durable pigments are characterized in that no more than about 25% of the pigment dissolves in sulfuric acid in the acid solubility test as described below, and that silicon dioxide represents at least about 1.4% of the total weight of the pigment for an average particle size of 250 nanometers.

A durable pigment can be produced by the process of the present disclosure when at least 85% of the titanium dioxide particles have a full, complete surface coverage. It is typical that at least 95% of the titanium dioxide particles having full, complete surface coverage, and a fraction of about 98% or more is even more typical, most typically at least about 99% of the particles have full, complete surface coverage.

The process of this disclosure can also be used to treat subpigmentary titanium dioxide particles. Subpigmentary titanium dioxide particles, also referred to as nano-sized titanium dioxide particles, typically have an average size ranging from about 10 to about 200 nanometers, typically from about 20 to about 150 nanometers. Due to higher surface area of subpigmentary titanium dioxide particles, higher amounts of silicon dioxide treatments will be needed to provide durability. Methods for calculating the amount of silicon dioxide for a given titanium dioxide particle size to provide durability equal to that for a pigmentary titanium dioxide are known to those skilled in the art. For example, based on particle size differences and differences in surface area, a 1.4% durable silicon dioxide treatment on a 250 nanometers particle translates to a 17.5% silicon dioxide treatment on a 20 nanometer particle.

A silicon oxide treatment on the $TiO_2$ particles may be amorphous silica. When a silicon dioxide composition is contacted with $TiO_2$ particles in the chloride process, the oxide treatment on the $TiO_2$ particles in this disclosure is a mixture of amorphous aluminum oxide and amorphous silicon dioxide. The thickness of the treatment layer deposited in the present disclosure is generally not more than about 4 nm.

The silicon dioxide composition ideally has a high solids content of silicon dioxide particles. Higher silicon dioxide content minimizes the amount of liquid medium to be evaporated. Typically, the silicon dioxide composition comprises 10-80% by weight (wt %) of silicon dioxide particles, more typically, 30-70 wt % of silicon dioxide particles. A typical silicon dioxide composition comprises at least about 50 wt % of silicon dioxide particles.

When the inorganic particle is titanium dioxide and the sinterable material is silicon dioxide, the liquid medium may be any suitable medium that will evaporate to enable generation of aerosol particles of silicon dioxide under conditions in which the silicon dioxide particles are contacted with titanium dioxide particles. Examples of suitable liquid media include water, titanium tetrachloride, or carbon tetrachloride. Typically, the medium is water due to ease of use and availability of high solids content aqueous slurries comprising silicon dioxide particles.

Typically, the pigment is more than 99% rutile.

The process of this typical embodiment of the disclosure provides titanium dioxide particles comprising a silicon dioxide treatment. The fraction of particles treated, having full, complete surface coverage can be determined by analysis of samplings of 1000 particles as described below. When at least 85% of the particles had full, complete surface coverage (FIGS. 3 and 4, based on Example 3, Samples B and E, respectively), the acid solubility of these particles was equal to that of durable, commercial grade products. Experience has shown that acid solubility of 25% or less, typically 20% or less, more typically 15% or less and most typically 10% or less, correlates with outdoor exposure required for commercial grade durable pigments. Thus, acid solubility serves as an accelerated durability test.

By, "full, complete coverage of the particles", it is meant that the entire surface of the titanium dioxide particle is covered with the layer of surface treatment. The product of the present disclosure is characterized by the fact that at least 85% of the particles can be fully and completely covered by a layer of surface treatment. This layer is thin and uniform. The thickness of the layer is about 1 to 4 nm for particles that are about 1% by weight aluminum oxide and 1.2% by weight silicon dioxide for pigmentary titanium dioxide particles. Higher concentrations of the surface treatment are expected to produce thicker layers, but at equal uniformity. Microscopic analysis of the product of Example 3, Samples B and E showed that about 85% or more of the pigment particles have a treatment layer thickness of 1 to 2.5 nm, while in less than about 5% of the pigment particles, the treatment layer is about 4 nm thick.

The inventors believe that it is the completeness of surface coverage resulting from the process of the present disclosure that may provide pigment durability meeting industry standards at treatment levels of about 2 to 3% of the total pigment weight for pigmentary titanium dioxide particles, compared to treatment levels of about 6% required for typical outdoor architectural durable grade titanium dioxide pigment.

In comparison to the present disclosure, wet treatment processes deposit silicon dioxide and aluminum oxide on to the surface of the pigment particle by precipitation. Wet treatment processes typically produce silica debris and irregularly treated particle surfaces.

Elimination of wet treatment offers an advantage in the overall titanium dioxide manufacturing process in reducing processing steps. New treatment compositions offer the potential to produce pigments having improved processing characteristics and properties.

In contrast to pigments produced by wet treatment processes, pigment produced by the process of this disclosure can be substantially free of debris. This lack of debris may contribute to improved dispersion and improved performance in treatments and plastics. Although some debris may be seen in FIG. 2, prepared according to Example 2, this is not unexpected due to incomplete mixing and other conditions present in the production of this Example.

In the typical embodiment of this disclosure, it is typical that the step of contacting silicon dioxide composition with titanium dioxide particles is performed under turbulent mixing conditions. The achievement of turbulent conditions is generally correlated in terms of the Reynolds number for the flow, which is the ratio of a characteristic length-velocity product to the kinematic viscosity. For pipeflow, the characteristic length is the pipe diameter and the characteristic velocity is the mean axial velocity. In stirred tanks, the characteristic length is the impeller diameter and the characteristic velocity is the product of the impeller diameter and the rotational frequency (revolutions per unit time). In pipeflow, it is generally recognized that the transition from laminar to turbulent flow begins at a Reynolds number of 2100-2300 and is complete near a Reynolds number of 4000. To ensure fully turbulent flow in a pipeline contactor, a Reynolds number of at least 5000 is typical for contacting slurry and particles. In properly baffled and agitated cylindrical stirred vessels, the turbulent condition is reached near a Reynolds number of 100, therefore a Reynolds number of at least 200 is typical.

There should also be sufficient residence time at a sufficiently high temperature to cause the silicon dioxide particles to sinter and form a treatment on the surface of the titanium dioxide particles. Using the relation for the characteristic sintering time of silicon dioxide found in Xiong, Y. and Pratsinis S. E. (*J. Aerosol Sci.*, 24 (3), 301-313 (1993)), one may calculate the time required for 99% coverage at various temperatures and initial particle sizes. Fractional coverage is defined as the projected area divided by the circumscribed projected area of two particles sintering into one. Table 1 provides calculated time requirements for both 10 and 20 nm diameter silicon dioxide particles at various temperatures:

TABLE 1

Time (in seconds) to Achieve 99% Coverage

| Temperature (° C.) | Initial Particle Diameter | |
| --- | --- | --- |
|  | 10 nm | 20 nm |
| 1500 | 1.2 | 2.4 |
| 1000 | 1.7 | 3.3 |
| 500 | 3.7 | 7.4 |

In addition to the time required for sintering, sufficient residence time is needed for the titanium dioxide particles to scavenge all of the silicon dioxide particles. This may be estimated as a multiple of 80 times the characteristic collision time. For submicron titanium dioxide particles and nanoscale silicon dioxide particles, this may be calculated from Brownian collision physics. The characteristic Brownian collision time for gases in the continuum regime is effectively independent of temperature. For a typical gas, it can be estimated as the quotient of $2 \times 10^9$ (seconds/cc) divided by the particle concentration (1/cc). The required residence time for sufficient collisions may be estimated as 80 times this or by the quotient of $1.6 \times 10^{11}$ (seconds/cc) divided by the particle concentration (1/cc). To decide whether collision or sintering is the determining factor in setting the residence time, one may define the critical particle concentration as the concentration where both time requirements are equal. That will occur at a particle concentration equal to the quotient of $1.6 \times 10^{11}$ (seconds/cc) divided by the required sintering time (seconds). For concentrations above critical particle concentration, the residence time is determined by sintering requirements. For concentrations below critical particle concentration, the residence time is determined by collision requirements. Using the times in Table 1 as an example, the corresponding critical particle concentrations are provided below in Table

TABLE 2

Example Critical Particle Concentrations (1/cc)

| Temperature (° C.) | Initial Particle Diameter | |
| --- | --- | --- |
|  | 10 nm | 20 nm |
| 1500 | $1.4 \times 10^{11}$ | $6.8 \times 10^{10}$ |
| 1000 | $9.6 \times 10^{10}$ | $4.8 \times 10^{10}$ |
| 500 | $4.3 \times 10^{10}$ | $2.2 \times 10^{10}$ |

Although pigment durability can be achieved at levels of silicon dioxide of about 1% by weight of a titanium dioxide pigment, higher levels of silicon dioxide may be deposited on the surface of a pigment of the present process. Higher levels of silicon dioxide as noted previously are needed to provide equal durability for subpigmentary $TiO_2$ particles.

In the present process when titanium dioxide is produced by the chloride process, titanium tetrachloride is preheated to a temperature of from about 300 to 650° C. and mixed with aluminum trichloride forming a chloride mix which is fed into a pre-heated stream of oxygen. The typical location for the addition of the aluminum trichloride is in a mixture with the titanium tetrachloride. This chloride mix may contain other metal compounds, used in the chloride pigment manufacture including compounds of boron, phosphorous, zirconium, and others. The introduction of phosphorous compounds into the oxidizer is generally positioned to control corrosion and may be at some point down stream of the point where titanium tetrachloride and aluminum trichloride are introduced into the reactor.

In the chloride process, according to the typical process of this disclosure, oxygen is present as an initial reactant and may also be added with the addition of the silicon dioxide composition. Although it is typical to run the present process with the oxygen in excess of the amount required to oxidize the chloride mix, the process may be operated with the concentration equal to or less than the stoichiometric amount.

The silicon dioxide composition is contacted with titanium dioxide particles according to the present disclosure at a temperature sufficient to evaporate the liquid medium and release the silicon dioxide particles as aerosol particles and cause the silicon dioxide aerosol particles to sinter to form a treatment on the titanium dioxide particles. Typically, when titanium dioxide is produced by the chloride process, the silicon dioxide composition is introduced at a point downstream of where titanium tetrachloride and oxygen are reacted so that at least 97% of the titanium tetrachloride has been converted to titanium dioxide particles. More typically the temperature is at least 1000° C. at the point that the silicon dioxide composition is introduced. The temperature may vary based on the size of the silicon dioxide particles as well as the liquid medium. The temperature may also vary depending upon the purge/quench ratio (mol $Cl_2$/mol $TiCl_4$) and percent excess oxygen as well as the residence time at temperature. It is believed that sufficient residence time at temperature can be important for sintering since, based on computer modeling of flue temperature profile and sintering kinetics, it has been found that for 10-20 nanometer silica particles sufficient residence time for sintering would be achieved by contacting the silicon dioxide composition at 1000° C. or higher.

For alternative processes wherein the inorganic particle is titanium dioxide and the sinterable material is silicon dioxide, but not including steps of the chloride process to produce titanium dioxide particles, a silicon dioxide composition may be contacted with titanium dioxide particles in batch, semi-continuous or continuous processes.

In the typical process, that is, when titanium dioxide is produced by the chloride process, the temperature at which the silicon dioxide composition is introduced is typically at a temperature wherein the conversion of titanium tetrachloride to titanium dioxide is nearly complete. For example, at least 97% of the titanium tetrachloride has been converted to titanium dioxide. That is, the point where not more than 3% of the titanium tetrachloride remains unreacted. From their work adding silicon tetrachloride in the vapor phase, the inventors have found that the point in the reactor where about 3% of the titanium tetrachloride is unreacted, the fraction of particles having full, complete coverage by the surface treatment is about 85%. At the point in the reactor where about 2% of the titanium tetrachloride is unreacted, the fraction of particles having full, complete coverage by the surface treatment is about 95%. At the point in the reactor where about 1% of the titanium tetrachloride is unreacted, the fraction of particles having full, complete coverage by the surface treatment is more than about 98%. The corresponding amount of titanium tetrachloride converted to titanium dioxide at these points is at least 97%, at least 98% and at least 99%, respectively. Extrapolating from these data, it is believed that the temperature for deposition in accordance with this disclosure should be below the temperature corresponding to the foregoing titanium tetrachloride conversions.

Sinterable materials other than silicon dioxide may be deposited on inorganic particles using the process of this disclosure. For example, in one alternative embodiment, a composition comprising a sinterable material may be contacted with zinc oxide during the process of producing zinc oxide from zinc metal by melting the metal, evaporating and oxidizing zinc in air in the vapor state. In another alternative embodiment, a composition comprising a sinterable material may be contacted with silica during the process of producing silica from a silicon halide, $SiX4$ (where X=F, Cl), by flame hydrolysis where the silicon halide is decomposed in the presence of oxygen.

The products produced by the process of this disclosure may be treated with organic treatments as is known by one skilled in this art.

Test Methods

Acid Solubility is determined as the amount of pigment that dissolves in hot concentrated sulfuric acid. In this test method, a small sample of pigment was placed in hot sulfuric acid (about 175° C.) and digested for an hour. The sample was then diluted with a measured amount of water and all particulate material was filtered out. A measured sample of the filtrate was then placed in a volumetric flask. Hydrogen peroxide was added to the flask to ensure all the titanium ions were in the proper oxidation state for their concentration to be determined spectrophotometrically at 400 nm. The flask was then filled to volume with 10% sulfuric acid. The absorbance was measured vs. a blank containing the same amount of hydrogen peroxide as was added to the sample in 10% sulfuric acid. The percent of titanium dioxide was read from a calibration curve prepared from known standards.

High Resolution Electron Microscopy Procedures:

A combination of high resolution transmission EM (HREM) with atomic resolution and high resolution low voltage scanning EM (LVSEM) was used to determine the microstructure, morphology, treatment layer thickness, uniformity and chemical composition. Herein, "EM" means electron microscopy or electron microscope.

Microstructure and high precision chemical compositional analyses on a (sub)nanometer scale were carried out by HREM and the associated electron stimulated energy dispersive X-ray compositional spectroscopy (EDX), respectively. A Philips CM200 field emission gun HREM/ScanningTEM (STEM), Philips CM20 HREM and a modified Philips CM30 environmental-HREM instruments were used in the investigations, with an accelerating voltage of 200 kV (ref: P.L. Gai, DuPont: published in Advanced Materials, Vol. 10, p. 1259, 1998). All the EMs were equipped with X-ray spectrometers to analyze chemical composition.

The extent of treatment and treatment layer coverage observations were made on all sides (including top and bottom surfaces) of the particles using standard sample tilting methods. For HREM, the pigment crystals were oriented so that the desired crystal axes (e.g. <010>) were exactly parallel to the electron beam. Primary magnifications were 100,000 to 750,000.

A minimum sampling of 1000 particles having variable particle size and dimensionality was studied to represent an accurate measure of the fraction of particles treated and the extent of the treatment surface coverage. HREM at atomic resolution was used to determine monolayer treatments as well as nanometers-scale treatments. Observations of fully treated particles (with regularity in treatment layers) and of partially treated particles (with irregularity in treatment layers) were carried out. Histograms were prepared according to standard statistical methods to determine the fraction of particles where the treatment layer was full and complete at treatment layer thickness.

EXAMPLE 1

Titanium tetrachloride was introduced into a tubular reactor comprising three concentric tubes and an area above the tubes, by bubbling oxygen at 1 l/min through a cylinder of liquid titanium tetrachloride at room temperature where it reacted in the presence of 2 0 methane. The titanium tetrachloride stream was introduced through the center tube. Methane flowed through the inner annulus at a rate of 0.5 l/min. Additional oxygen was provided through the outer annulus at 3 l/min. A simple diffusion flame resulted. Based on these flows, an adiabatic flame temperature of 2108° C. was calculated. $TiO_2$ particles were formed in the flame. The product was collected on a sintered metal filter.

A silicon dioxide slurry was prepared by adding 10 ml of deionized water to 0.2 g of silicon dioxide, EP7965 grade, M5

Cab-o-sil, aerogel silica, available from Eager Plastics, Inc. Aggregate particle size was 200-300 nm, with an average primary particle size of less than 20 nm. The silicon dioxide slurry was atomized using a gas assisted atomizer (Baxter Healthcare) using argon as the carrier gas. The aerosol so obtained was introduced into an area of the tubular reactor above where titanium tetrachloride reacted with the oxygen and methane, that is, downstream of the flame. The temperature after water evaporation and dilution was calculated as 1008° C.

FIG. 1 is an electron micrograph of the treated titanium dioxide particles produced in this Example. As can be seen, particles bear relatively uniform treatments.

EXAMPLE 2

Atomic resolution in situ (environmental) transmission electron microscopy (ETEM) was used to observe dynamic treatment of titanium dioxide pigment particles with silicon dioxide particles. For this example, an atomic resolution ETEM (see P. L. Gai, Advanced Materials, Vol. 10, p. 1259, 1998) was used. The instrument was a Philips CM30 electron microscope, operating at 200 keV. A microreactor was fitted inside the column of the instrument. A sample stage with a furnace allowed samples to be heated to different temperatures. Very low dose electron beam currents were used for the dynamic imaging reacting materials. The image signal was amplified by a low light television camera connected to a video recording system to capture the dynamic sequences. Calibration, "blank" experiments, that is, without the electron beam, were carried out on a different set of samples, with the beam switched on for a few seconds, to record the image and checked with in situ data.

For the in situ experiments, the movement of silicon dioxide particles (EP7965 grade, M5 Cab-o-sil, aerogel silica) was monitored from room temperature to about 900° C. The direct observations showed silicon dioxide treatments on exposed titanium dioxide particle surfaces. The chemical composition analyses of the titanium dioxide pigment particles after exposure to the silicon dioxide particles and the nanoscale treatments were performed using electron stimulated energy dispersive X-ray compositional spectroscopy (EDX), to provide high spatial resolution on the (sub) nanometer scale.

Figure 2:
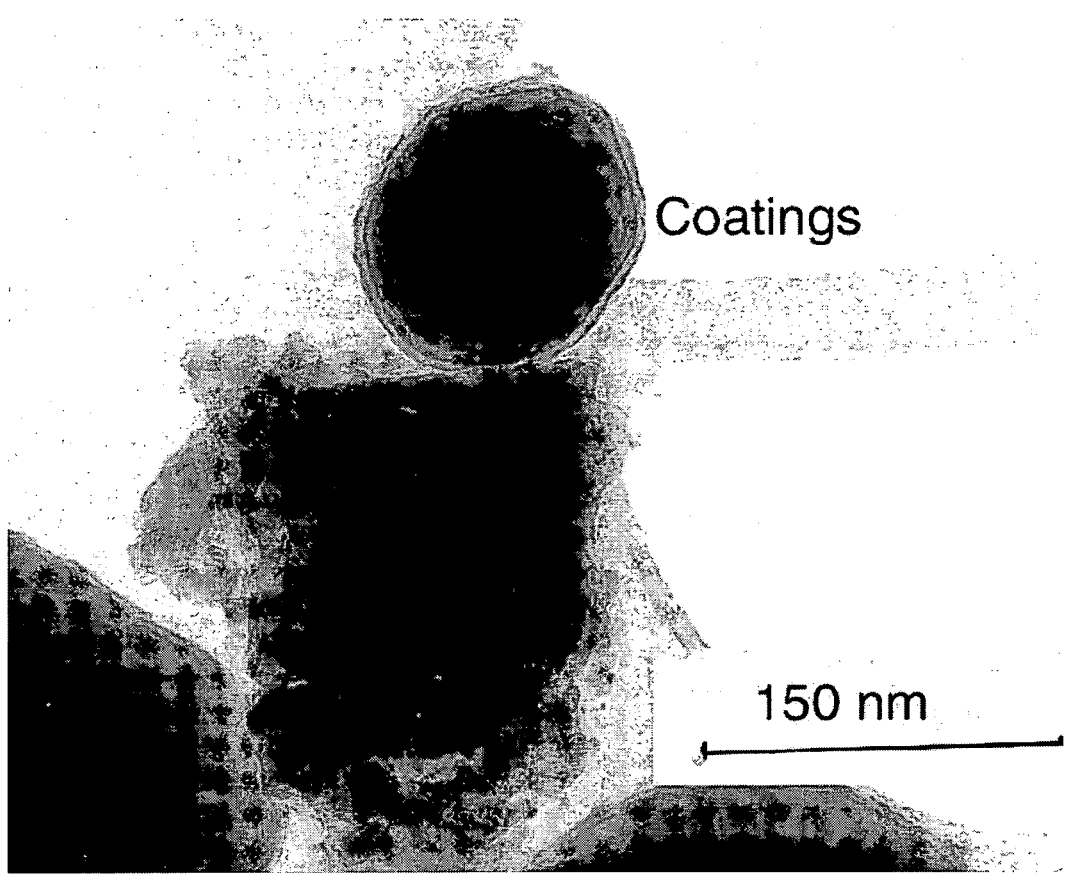
FIG. 2 is an electron micrograph of the titanium dioxide pigment particles produced in Example 2.

FIG. 2 is an electron micrograph of the treated $TiO_2$ particles produced in this Example. As can be seen, particles bear treatments, although treatments are not as uniform as in FIG. 1. However, this is not unexpected based on the nature of the experiment. In this example, no mixing or other means of introducing turbulence to enhance contact of the silicon dioxide particles with the titanium dioxide particles was provided in the electron microscope.

EXAMPLE 3

A series of titanium dioxide pigments were treated with silica using a colloidal silicon dioxide slurry as the silica source. These pigments were prepared to illustrate the ability of silicon dioxide particles to provide treatments on $TiO_2$ particles with greater than 85% of $TiO_2$ particles treated and to produce sufficient quantities of treated particles to measure acid solubility.

To prepare the samples in this Example, 10 grams of an untreated titanium dioxide pigment, produced by the chloride process, having a CBU of about 11-12, was slurried in 10 grams of water in a polyethylene bottle. CBU is defined in U.S. Pat. No. 5,759,511, and references cited therein. To prepare the treated pigments, 3.3 grams of a silicon dioxide slurry, optionally with a dispersant added as specified in Table 3, was added to the titanium dioxide slurry. The bottle was vigorously shaken for 30 seconds.

To Samples A, B, and C, an additional 10 grams of water was added to produce a better slurry. These Samples were placed in a 300° C. furnace and allowed to dry.

Samples D and E were partially dried at 70° C. in a convection oven for about one hour, and then placed in a furnace at 300° C. to dry.

After the Samples had dried, the temperature of the furnace was increased to a set point of 1100° C. Over a period of about 35 minutes, temperature increased from 500° C. to 1050° C. Samples were maintained at a temperature of about 1080° C. for 10 minutes and above 1050° C. for 20 minutes, before Samples were allowed to cool.

Samples were removed from the furnace at a nominal temperature of 400° C., and cooled in room temperature air. After cooling, each Sample was analyzed to measure acid solubility.

TABLE 3

| Sample No. | Dispersant | Acid Solubility |
|---|---|---|
| Control (a) | None | 31.8 |
| Control (b) | None | 22.2 |
| A | Acrylic block copolymer (c) | 7.11 |
| B | Nonionic graft polymer containing phosphated functionality (d) | 4.48 |
| C | Acrylic graft copolymer containing acid functionality (e) | 4.69 |
| D | Citric acid | 5.62 |
| E | None | 7.26 |

(a) Untreated pigment, that is, no silicon dioxide treatment, no calcination.
(b) Calcined pigment, but no silicon dioxide treatment.
(c) 10 BMA//5 MMA/10 MAA prepared via group transfer polymerization according to U.S. Pat. No. 5,221,334 where BMA = butyl methacrylate; MMA = methyl methacrylate; MAA = methacrylic acid; copolymer was neutralized with N,N-dimethylethanolamine.
(d) Prepared according to Polymer Dispersant 2 in U.S. Pat. No. 6,660,793.
(e) Prepared according to Polymer Dispersant 1 in U.S. Pat. Application US-2003-0108667-A1.

As can be seen from Table 3, the titanium dioxide pigments treated with silicon dioxide derived from silicon dioxide particles having an average primary particle size of less than 20 nm, can provide acid solubility sufficient to meet industry standards for durability.

Figure 3:
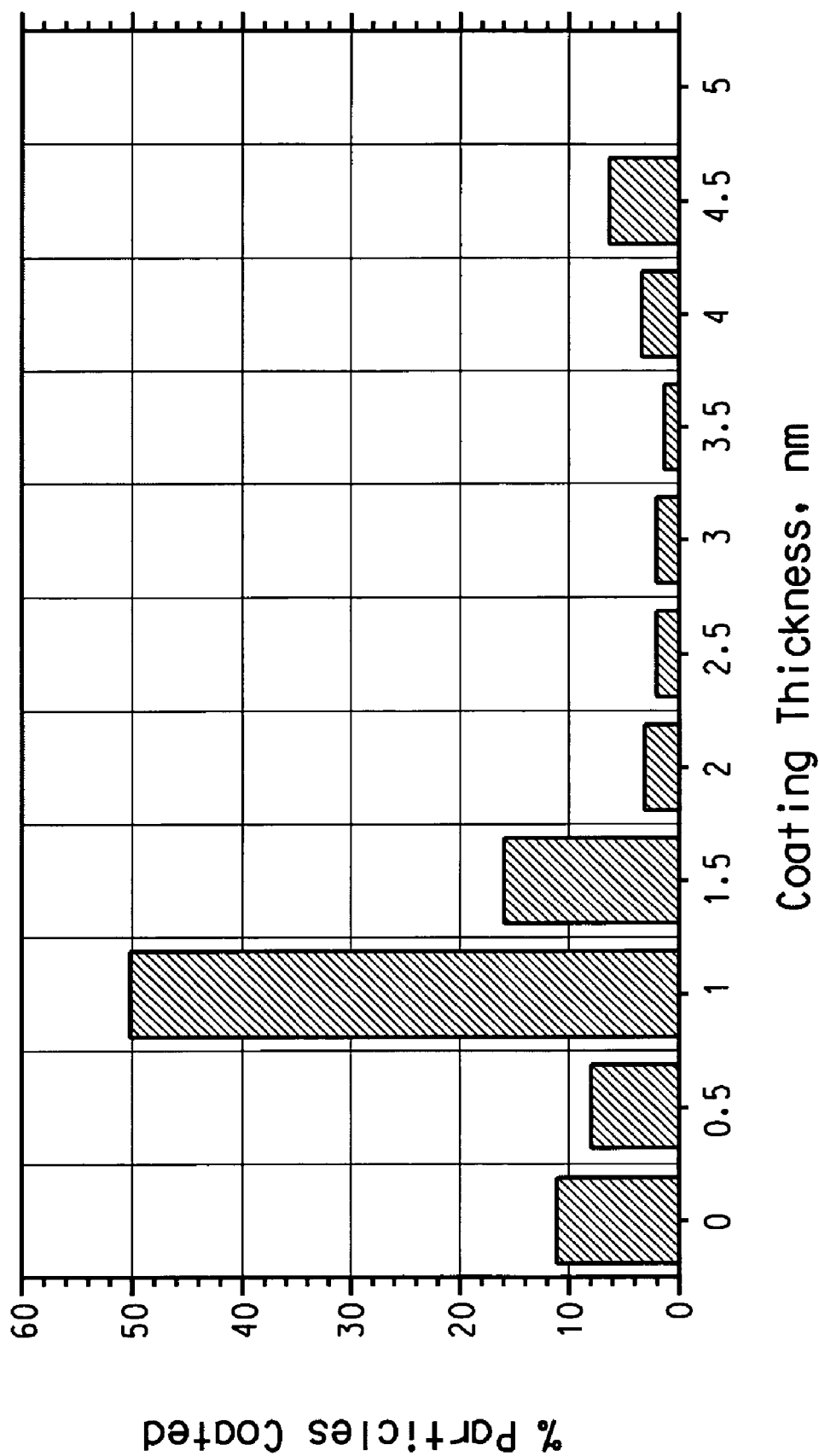
FIG. 3 is a histogram showing percent of titanium dioxide particles treated with silica based on Example 3, Sample B.
Figure 4:
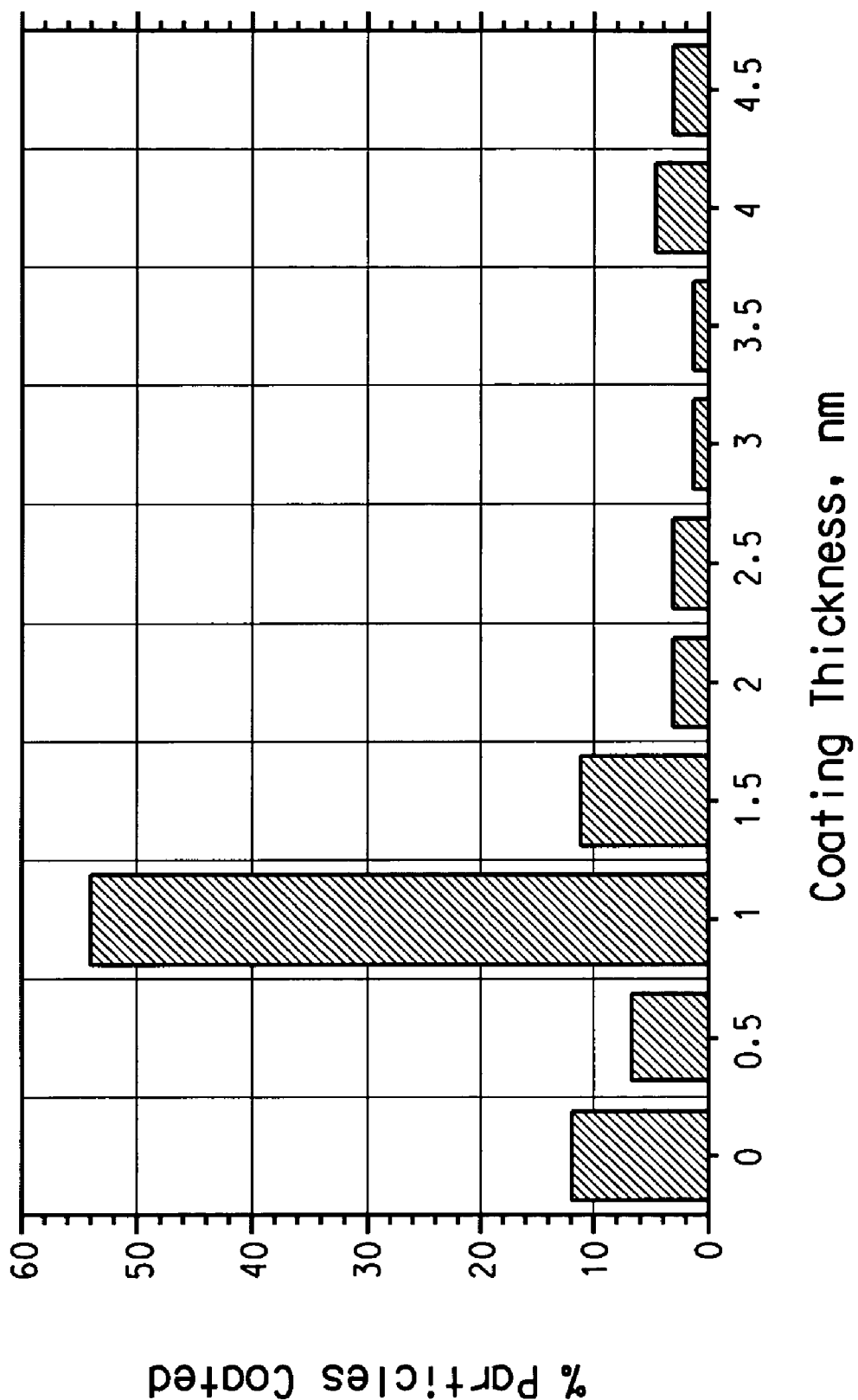
FIG. 4 is a histogram showing percent of titanium dioxide particles treated with silica based on Example 3, Sample E.

FIGS. 3 and 4 graphically illustrate the percent of particles treated in Samples B and E and thickness of the treatments. In these Figures, it can be seen that about 85% or more of the titanium dioxide particles have been treated. It should be noted that debris was also present in these samples. While the processes to produce these pigments differs from the process of this disclosure, these samples illustrate the potential for titanium dioxide particles treated with silicon dioxide derived from silicon dioxide particles to achieve equal, if not better acid solubility, and therefore, durability. Due to better, that is, more turbulent, mixing conditions and potential for higher temperatures for contacting the silicon dioxide particles with titanium dioxide particles according to this disclosure, it is anticipated that not only will greater than 85% of the particles be treated, but also that treatments will be more uniform, hence, better acid solubility and better durability.

What is claimed is:

1. A process for producing inorganic particles bearing a surface treatment, comprising, in order:
   (a) contacting inorganic particles with a composition consisting essentially of a liquid medium and a sinterable material selected from the group consisting of inorganic oxide and mixed oxide;

(b) forming aerosol particles of sintering material;
(c) sintering the aerosol particles of sinterable material onto the inorganic particles:
wherein steps (a), (b), and (c) occur at a temperature of at least 1000° C.

2. The process of claim 1 wherein the inorganic particles are oxides, carbonates, sulfates, titanates, arsenides, sulfides, selenides, phosphides, and combinations of two or more thereof.

3. The process of claim 2 wherein the inorganic particles are selected from the group of metal oxides and fumed silica.

4. The process of claim 3 wherein the metal oxide is selected from the group of titanium dioxide and zinc oxide.

5. The process of claim 1 wherein the contacting step occurs in an oxygenation process to form a treatment on the inorganic particles.

6. The process of claim 5 wherein the inorganic particle is titanium dioxide.

7. The process of claim 1 wherein the inorganic particles have an average particle size in the range of about 200 to 1000 nanometers.

8. The process of claim 7 wherein the inorganic particles have an average particle size in the range of about 200 to 500 nanometers.

9. The process of claim 1 wherein the inorganic particles have an average particle size in the range of from about 10 to about 200 nanometers.

10. The process of claim 9 wherein the inorganic particles have an average particle size in the range of from about 20 to about 150 nanometers.

11. The process of claim 1 wherein the inorganic oxide is selected from the group of silica, alumina, phosphorous oxide, boron oxide, magnesium oxide, niobium oxide, germanium oxide, zirconium oxide and zinc oxide.

12. The process of claim 1 wherein the sinterable material is present in the composition in the form of particles.

13. The process of claim 12 wherein the sinterable material has a particle size of less than 100 nanometers.

14. The process of claim 13 wherein the sinterable material has a particle size of at least 5 nanometers.

15. The process of claim 13 wherein the sinterable material has a particle size of less than 50 nanometers.

16. The process of claim 15 wherein the sinterable material has a particle size of less than 20 nanometers.

17. The process of claim 12 wherein the sinterable material is silica or alumina.

18. The process of claim 17 wherein the composition comprising a sinterable material is a silicon dioxide slurry comprising silicon dioxide particles of 10-20 nanometers in size and water as the liquid medium.

19. A process for producing titanium dioxide particles bearing a surface treatment, comprising, in order:
(a) reacting titanium tetrachloride vapor stream with at least a stoichiometric amount of oxygen in a plug flow reactor to form a product stream comprising titanium dioxide particles:
(b) contacting the titanium dioxide particles with a composition consisting essentially of a liquid medium and a sinterable material selected from the group consisting of inorganic oxide and mixed oxide
(c) forming aerosol particles of sintering material;
(d) sintering the aerosol particles of sinterable material onto the inorganic particles: wherein steps (b), (c), and (d) occur at a temperature of at least 1000° C.

20. The process of claim 19 wherein the titanium tetrachloride vapor stream further comprises aluminum chloride.

21. The process of claim 20 wherein before the introduction of the composition comprising sinterable particles, at least 97% of the titanium tetrachloride has been converted to titanium dioxide.

22. The process of claim 21 wherein at least 98% of the titanium tetrachloride has been converted to titanium dioxide.

23. The process of claim 22 wherein at least 99% of the titanium tetrachloride has been converted to titanium dioxide.

24. The process of claim 19 wherein the sinterable material is silicon dioxide.

25. The process of claim 24 wherein the titanium dioxide particles have an average particle size in the range of about 200 to about 1000 nanometers.

26. The process of claim 25 wherein the titanium dioxide particles have an average particle size in the range of about 200 to about 500 nanometers.

27. The process of claim 24 wherein the titanium dioxide particles have an average particle size in the range of from about 10 to about 200 nanometers.

28. The process of claim 24 wherein the titanium dioxide particles have an average particle size in the range of from about 20 to about 150 nanometers.

29. The process of claim 24 wherein the process produces a durable pigment wherein at least 85% of the titanium dioxide particles have a full, complete surface coverage.

30. The process of claim 29 wherein at least 95% of the titanium dioxide particles have a full, complete surface coverage.

31. The process of claim 30 wherein at least 98% of the titanium dioxide particles have a full, complete surface coverage.

32. The process of claim 31 wherein at least 99% of the titanium dioxide particles have a full, complete surface coverage.

33. The process of claim 24 wherein the silicon dioxide is at least about 1.4% of the total weight of the pigment and wherein the pigment has an average particle size of 250 nanometers.

34. The process of claim 24 wherein the silicon dioxide is at least about 17.5% of the total weight of the pigment and wherein the pigment has an average particle size of 20 nanometers.

35. The process of claim 24 wherein the sinterable material comprises 10-80% by weight (wt %) of silicon dioxide.

36. The process of claim 35 wherein the sinterable material comprises 30-70 wt % of silicon dioxide.

37. The process of claim 36 wherein the sinterable material comprises at least about 50 wt % of silicon dioxide.

38. The process of claim 24 wherein the liquid medium is water, titanium tetrachloride or carbon tetrachloride.

39. The process of claim 24 wherein the silicon dioxide composition is contacted with titanium dioxide particles under turbulent mixing conditions.

40. The process of claim 39 wherein the contacting occurs at a Reynolds number of at least 200.

* * * * *